(12) United States Patent
Chobotov

(10) Patent No.: US 8,978,448 B2
(45) Date of Patent: Mar. 17, 2015

(54) IN VITRO TESTING OF ENDOVASCULAR DEVICE

(71) Applicant: Trivascular, Inc., Santa Rosa, CA (US)

(72) Inventor: Michael V. Chobotov, Santa Rosa, CA (US)

(73) Assignee: Trivascular, Inc., Santa Rosa, CA (US)

( * ) Notice: Subject to any disclaimer, the term of this patent is extended or adjusted under 35 U.S.C. 154(b) by 337 days.

(21) Appl. No.: 13/649,066

(22) Filed: Oct. 10, 2012

(65) Prior Publication Data

US 2013/0090715 A1 Apr. 11, 2013

Related U.S. Application Data

(60) Provisional application No. 61/545,978, filed on Oct. 11, 2011.

(51) Int. Cl.
*G01M 3/26* (2006.01)
*A61F 2/958* (2013.01)
*A61F 2/95* (2013.01)

(52) U.S. Cl.
CPC .......... *G01M 3/26* (2013.01); *A61F 2002/9522* (2013.01)
USPC ...................................... 73/40.5 R

(58) Field of Classification Search
CPC ........... G01M 3/26; G01M 3/36; A61F 2/958; A61F 2002/9522; A61F 2/95; A61M 2025/0177; A61M 2039/062
See application file for complete search history.

(56) References Cited

U.S. PATENT DOCUMENTS

| | | | |
|---|---|---|---|
| 3,991,767 A | 11/1976 | Miller et al. | |
| 4,140,126 A | 2/1979 | Choudhury | |
| 4,183,102 A | 1/1980 | Guiset | |
| 5,156,620 A | 10/1992 | Pigott | |
| 5,219,355 A | 6/1993 | Parodi et al. | |
| 5,327,774 A * | 7/1994 | Nguyen et al. | 73/37 |
| 5,330,528 A | 7/1994 | Lazim | |
| 5,370,691 A | 12/1994 | Samson | |
| 5,464,419 A | 11/1995 | Glastra | |
| 5,507,770 A | 4/1996 | Turk | |
| 5,534,024 A | 7/1996 | Rogers et al. | |
| 5,545,135 A | 8/1996 | Iacob et al. | |
| 5,554,180 A | 9/1996 | Turk | |
| 5,591,229 A | 1/1997 | Parodi | |
| 5,649,978 A | 7/1997 | Samson | |
| 5,670,708 A * | 9/1997 | Vilendrer | 73/37 |
| 5,697,968 A | 12/1997 | Rogers et al. | |
| 5,785,679 A | 7/1998 | Abolfathi et al. | |

(Continued)

FOREIGN PATENT DOCUMENTS

WO    WO 00/51522    9/2000
WO    WO 11/100367    8/2011

OTHER PUBLICATIONS

Cooley, "Surgical Treatment of Aortic Aneurysms," M.D., published in 1986 by W. B. Saunders Company.

(Continued)

*Primary Examiner* — David A Rogers
(74) *Attorney, Agent, or Firm* — Anderson IP, Inc.

(57) ABSTRACT

Some embodiments relate in part to endovascular devices such as prostheses and methods of testing same prior to deployment. Some embodiments may be directed more specifically to inflatable grafts or stent grafts and methods of in vitro leak testing of such grafts prior to in vivo deployment.

23 Claims, 6 Drawing Sheets

(56) References Cited

U.S. PATENT DOCUMENTS

| | | | |
|---|---|---|---|
| 5,843,160 A | 12/1998 | Rhodes | |
| 5,871,537 A | 2/1999 | Holman et al. | |
| 6,143,015 A | 11/2000 | Nobles | |
| 6,231,562 B1 | 5/2001 | Khosravi et al. | |
| 6,334,867 B1* | 1/2002 | Anson | 623/1.13 |
| 6,395,019 B2 | 5/2002 | Chobotov | |
| 6,602,280 B2 | 8/2003 | Chobotov | |
| 6,706,064 B1 | 3/2004 | Anson | |
| 6,733,521 B2 | 5/2004 | Chobotov et al. | |
| 6,761,733 B2 | 7/2004 | Chobotov et al. | |
| 6,776,604 B1 | 8/2004 | Chobotov et al. | |
| 7,090,693 B1 | 8/2006 | Chobotov et al. | |
| 7,125,464 B2 | 10/2006 | Chobotov et al. | |
| 7,254,988 B2* | 8/2007 | Keeble | 73/37 |
| 7,621,192 B2* | 11/2009 | Conti et al. | 73/865.6 |
| 7,840,393 B1 | 11/2010 | Whirley et al. | |
| 8,196,478 B2* | 6/2012 | Lorenz et al. | 73/856 |
| 8,431,145 B2* | 4/2013 | Toner et al. | 424/422 |
| 8,490,504 B2* | 7/2013 | Weinberg et al. | 73/865.6 |
| 2003/0066338 A1* | 4/2003 | Michalsky et al. | 73/37 |
| 2003/0110830 A1* | 6/2003 | Dehdashtian et al. | 73/37 |
| 2004/0016301 A1* | 1/2004 | Moreno et al. | 73/849 |
| 2005/0027347 A1 | 2/2005 | Chobotov et al. | |
| 2005/0090804 A1 | 4/2005 | Chobotov et al. | |
| 2006/0233990 A1 | 10/2006 | Humphrey et al. | |
| 2006/0233991 A1 | 10/2006 | Humphrey et al. | |
| 2007/0088255 A1* | 4/2007 | Toner et al. | 604/96.01 |
| 2009/0198267 A1 | 8/2009 | Evans et al. | |
| 2010/0030183 A1* | 2/2010 | Toner et al. | 604/500 |
| 2011/0307046 A1* | 12/2011 | Bourang et al. | 623/1.11 |
| 2012/0022636 A1 | 1/2012 | Chobotov | |
| 2012/0191174 A1 | 7/2012 | Vinluan et al. | |
| 2013/0013048 A1* | 1/2013 | Toner et al. | 623/1.11 |
| 2013/0297000 A1* | 11/2013 | Toner et al. | 623/1.11 |
| 2014/0230225 A1* | 8/2014 | Van Sciver | 29/468 |

OTHER PUBLICATIONS

Lawrence, Jr. et al. in "Percutaneous Endovascular Graft: Experimental Evaluation", Radiology vol. 163, No. 2, (May 1987), pp. 357-360.

Mirich et al. in "Percutaneously Placed Endovascular Grafts for Aortic Aneurysms: Feasibility Study," Radiology vol. 170, No. 3, Part 2, (Mar. 1989), pp. 1033-1037.

* cited by examiner

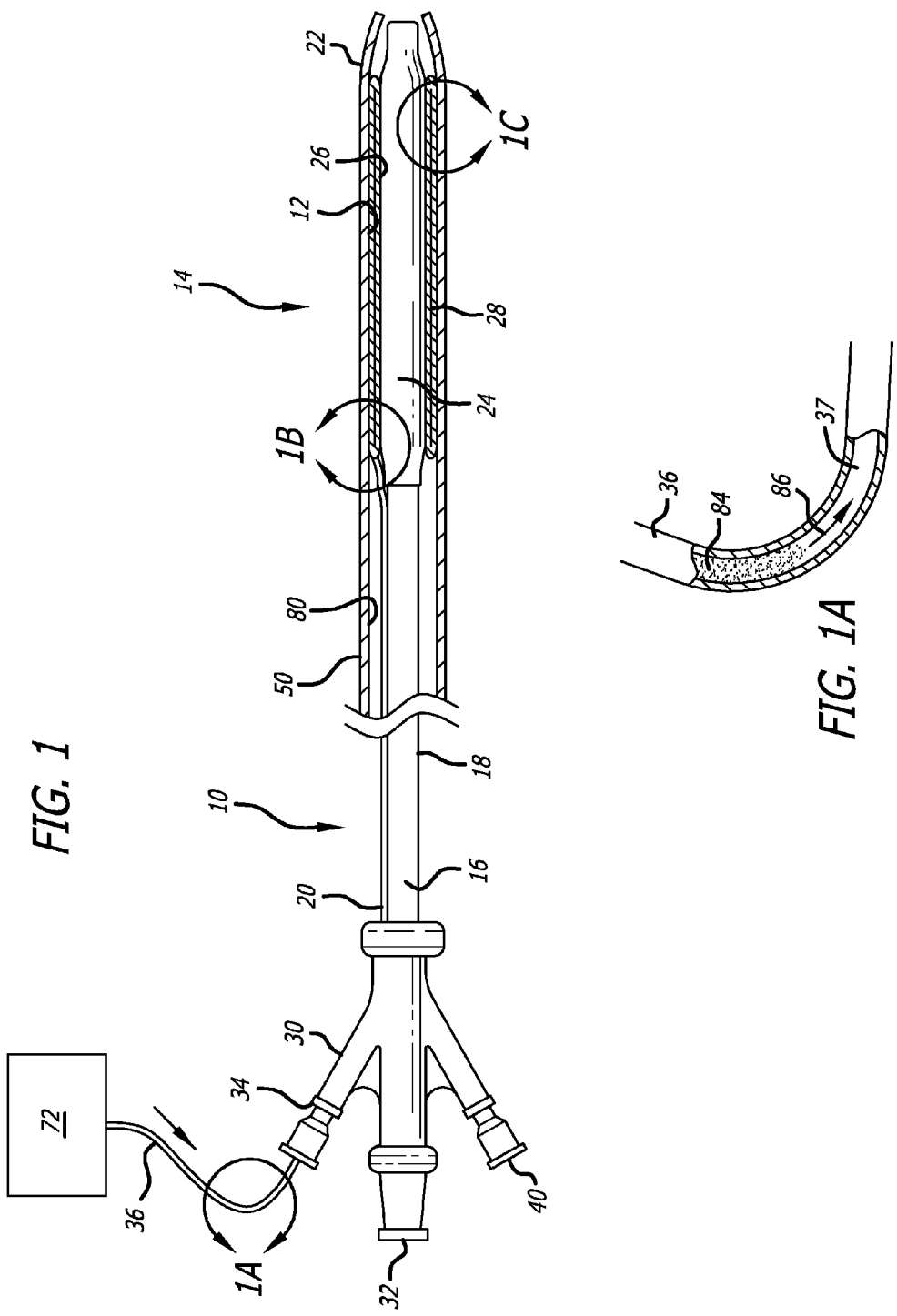

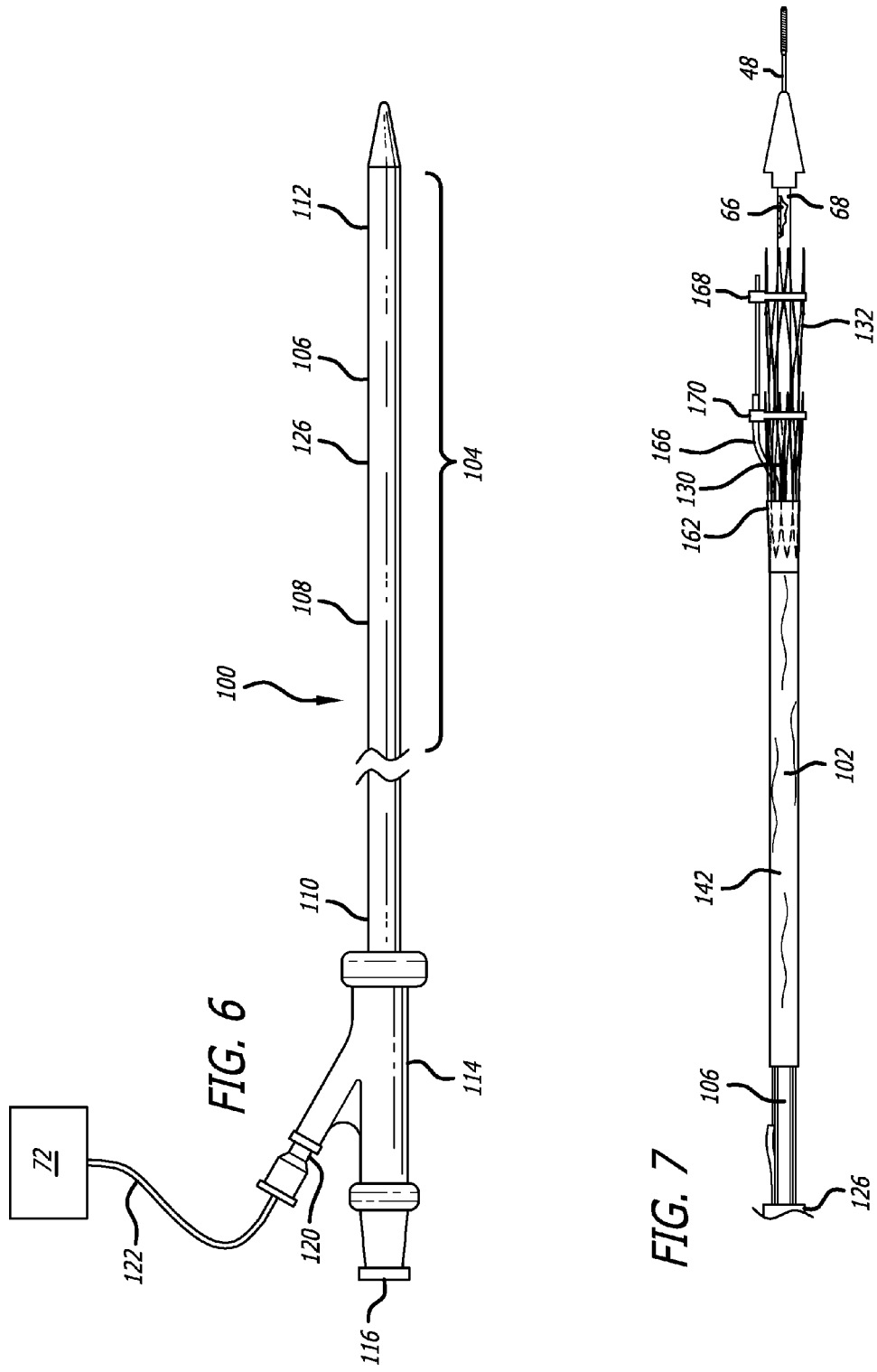

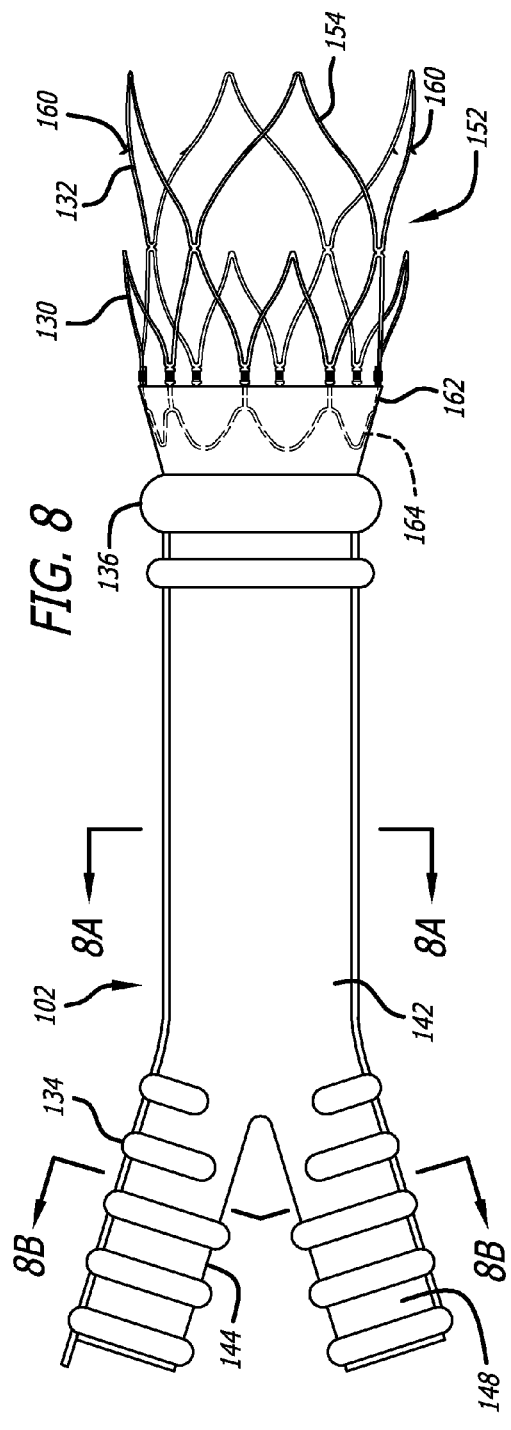

US 8,978,448 B2

IN VITRO TESTING OF ENDOVASCULAR DEVICE

RELATED APPLICATIONS

This application claims priority under 35 USC 119(e) from U.S. Provisional Patent Application Ser. No. 61/545,978, filed Oct. 11, 2011, by M. Chobotov, titled "IN VITRO TESTING OF ENDOVASCULAR DEVICE", which is incorporated by reference herein in its entirety.

FIELD OF THE INVENTION

Some embodiments relate in part to endovascular prostheses and methods of testing and deploying same. Embodiments may be directed more specifically to stent grafts and methods of making and deploying same within the body of a patient.

BACKGROUND

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of a AAA is described in a book titled Surgical Treatment of Aortic Aneurysms by Denton A. Cooley, M.D., published in 1986 by W. B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the AneuRx® stent graft manufactured by Medtronic, Inc. of Minneapolis, Minn., the Zenith® stent graft system sold by Cook, Inc. of Bloomington, Ind., the PowerLink® stent-graft system manufactured by Endologix, Inc. of Irvine, Calif., and the Excluder® stent graft system manufactured by W. L. Gore & Associates, Inc. of Newark, Del. A commercially available stent graft for the treatment of TAAs is the TAG™ system manufactured by W. L. Gore & Associates, Inc.

When deploying devices by catheter or other suitable instrument, it is advantageous to have a flexible and low profile stent graft and delivery system for passage through the various guiding catheters as well as the patient's sometimes tortuous anatomy. Some endoprosthesis embodiments delivered percutaneously by such catheter systems may also include an inflatable portion. Such an inflatable portion may be used to allow delivery in a low profile un-inflated state and be inflated in situ at a deployment site. Inflation at the deployment site may be used to expand, conform or otherwise remodel the inflatable portion of the endoprosthesis to achieve a seal or conformance with the interior profile of the vascular site being treated. What have been needed are reliable devices and methods for testing the integrity of the inflatable portion of an endoprosthesis after it has been loaded on a delivery catheter.

SUMMARY

Some embodiments are directed to a method of in vitro testing of an endovascular prosthesis, including providing an endovascular prosthesis including an inflatable portion which is loaded onto a delivery system, the inflatable portion of the endovascular prosthesis being in an uninflated state and including an interior volume bounded by at least one flexible layer of material. An inflatable portion of the prosthesis is inflated through a fill tube with a sterile removable inflation material and the fill material maintained at a pressure higher than ambient pressure with the delivery system in a deployment ready configuration. The delivery system and endovascular prosthesis are inspected for leaks of fill material. After confirming that there are no leaks in the inflatable portion of the prosthesis the inflation material may be removed from the inflatable portion. In some circumstances, the inflation material may be removed prior to confirming that there are no leaks or even if some leakage is detected. If leaks are detected, the delivery system may be repaired or replaced depending on the particular circumstances.

Some embodiments of a method of in vitro testing of an endovascular prosthesis include providing a double walled endovascular prosthesis including a toroidal inflatable portion which is loaded onto a delivery system, the inflatable portion of the endovascular prosthesis being in an uninflated state and including an interior volume bounded by at least one flexible layer of material. An inflatable portion of the prosthesis is inflated through a fill tube with a sterile removable inflation material and the inflation material maintained at a pressure higher than atmospheric pressure with the delivery system in a deployment ready configuration. The delivery system and endovascular prosthesis are inspected for leaks of inflation material. An absence of leaks in the inflatable portion of the prosthesis may then be confirmed and the inflation material removed from the inflatable portion.

Some embodiments of a method of in vitro testing of an endovascular prosthesis, include providing an endovascular prosthesis including an inflatable portion, the endovascular prosthesis being loaded onto a delivery system, the inflatable portion of the endovascular prosthesis being in an uninflated state and including an interior volume bounded by at least one flexible layer of material, a longitudinal inflation channel and an inflatable cuff disposed at a proximal end of the prosthesis and including an interior volume in fluid communication with an interior volume of the longitudinal inflation channel. An inflatable portion of the prosthesis may be inflated through a fill tube with a sterile removable inflation material and the inflation material maintained at a pressure higher than ambient pressure with the delivery system in a deployment ready configuration. The delivery system and endovascular prosthesis may be inspected or otherwise observed for leaks of inflation material. Once it is confirmed that there are no leaks in the inflatable portion of the prosthesis, the inflation material may be removed from the inflatable portion. In some instances, the inflation material may be removed in whole or part even if leaks are detected. In addition, in some instances, the inflation material or portions thereof may be left in place regardless of whether any leaks are detected.

Certain embodiments are described further in the following description, examples, claims and drawings.

BRIEF DESCRIPTION OF THE DRAWINGS

FIG. 1 illustrates an elevation view of an embodiment of a delivery system including an inflatable endovascular prosthesis loaded onto a delivery catheter embodiment.

FIG. 1A shows an enlarged view in partial section of a tubular member and fill material therein of FIG. 1 at the encircled portion 1A of FIG. 1.

FIG. 6 shows an elevation view of an embodiment of a delivery catheter which is configured to deploy an endovascular prosthesis.

FIG. 7 illustrates the delivery catheter embodiment of FIG. 6 with an outer sheath of the delivery catheter retracted revealing an embodiment of an inflatable endovascular prosthesis loaded onto a distal section of the delivery catheter in a constrained uninflated state.

FIG. 8 is an elevation view of the endovascular prosthesis of FIG. 7 in an expanded inflated state.

FIG. 8A is a transverse cross sectional view of the prosthesis of FIG. 8 taken along lines 8A-8A of FIG. 8.

FIG. 8B is a transverse cross sectional view of the prosthesis of FIG. 8 taken along lines 8B-8B of FIG. 8.

The drawings illustrate embodiments of the invention and are not limiting. For clarity and ease of illustration, the drawings are not made to scale and, in some instances, various aspects may be shown exaggerated or enlarged to facilitate an understanding of particular embodiments.

DETAILED DESCRIPTION

Embodiments discussed herein may be directed generally to methods and devices for testing of inflatable prosthesis that may be implanted into a patient's vascular system. Endovascular prostheses, such as stent grafts, and particularly, inflatable stent grafts, are often implanted in a patient's vasculature on a permanent or long term basis. Some delivery method embodiments are difficult or impossible to reverse beyond a certain point in an implant procedure and surgery may be required to remove a device that does not meet certain performance standards. For inflatable endovascular prosthesis that may be inflated within a patient's body lumen, such as the vessels of the patient's vasculature, it may be important to test an inflatable portion of the prosthesis for any leakage prior to deployment. In addition, some prosthesis, or portions thereof, may be delicate and care should be taken while loading such a device onto a delivery system prior to packaging, sterilization and shipment. Because of these factors, it may be desirable to test an inflatable portion of an inflatable endovascular prosthesis for leaks in the inflatable portion of the endovascular prosthesis after it has been loaded onto a delivery system. By this method, the inflatable portion of the endovascular prosthesis is tested for any leaks or imperfections after the manipulation of the prosthesis has occurred during the loading process and when little or no further manipulation of the device will occur prior to sterilization, shipment or both.

With regard to the endovascular prostheses portion of the delivery system embodiments discussed herein, the term "proximal" refers to a location towards a patient's heart and the term "distal" refers to a location away from the patient's heart. With regard to delivery catheter embodiments of the delivery systems discussed herein and components thereof, the term "distal" refers to a location that is disposed away from an operator who is using the catheter and the term "proximal" refers to a location towards the operator.

Figure 1B:
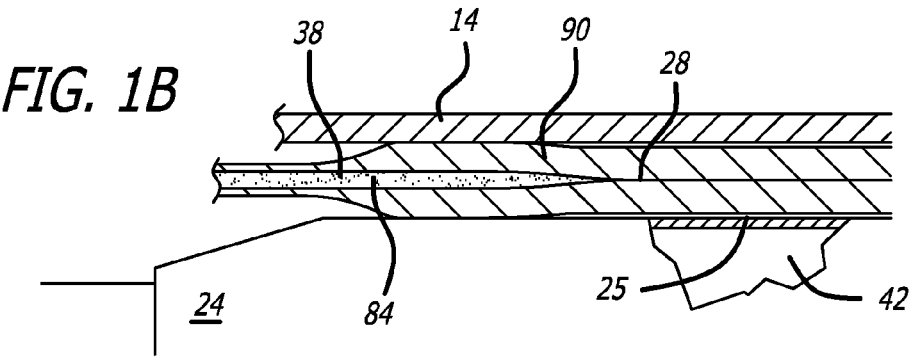
FIG. 1B shows an enlarged view in partial section of the prosthesis of FIG. 1 and fill material entering an interior volume thereof at the encircled portion 1B of FIG. 1.
Figure 1C:
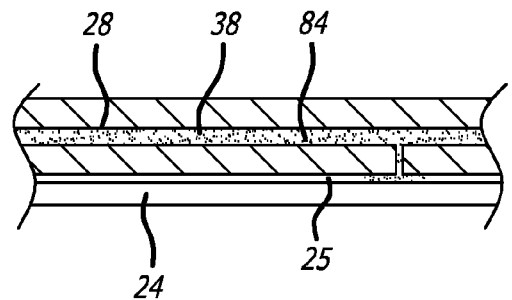
FIG. 1C shows an enlarged view in partial section of the prosthesis of FIG. 1 and fill material leaking from an interior volume thereof at the encircled portion 1C of FIG. 1.
Figure 1D:
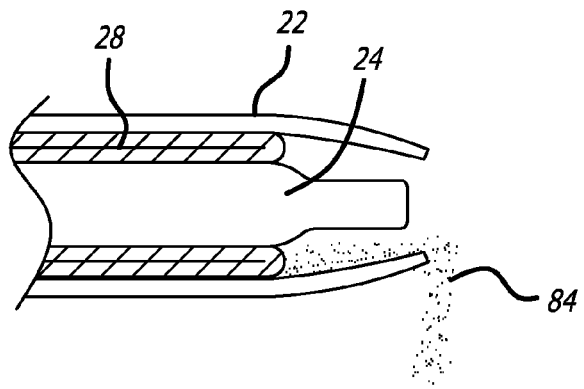
FIG. 1D shows an enlarged view in partial section of the prosthesis of FIG. 1 and fill material leaking from an interior volume thereof at a distal end of the delivery catheter embodiment of FIG. 1.

FIG. 1 illustrates a delivery system 10 including an inflatable endovascular prosthesis 12 loaded on a distal section 14 of a delivery catheter 16. The delivery system 10 is shown configured for clinical use and ready to deploy the endovascular prosthesis 12 but prior to packaging and shipment. The delivery catheter 16 of the delivery system 10 includes an elongate shaft 18 having a proximal end 20, a distal end 22 and a distal section 14. An expandable member in the form of an inflatable balloon 24 is disposed on the distal section 14 of the elongate shaft 18 within an inner lumen 26 of an inflatable portion 28 of endovascular prosthesis 12. The inflatable balloon 24 may be configured to be expanded and maintain the inner lumen 26 of the inflatable portion 28 of the prosthesis 12 during inflation of the inflatable portion 28. A proximal adapter 30 is secured to a proximal end 20 of the elongate shaft 18 and may include one or more ports configured to communicate with the various ports and lumens of the delivery catheter. For example, a guidewire port 32 may be disposed in communication with a guidewire lumen, a first inflation port 34 may be disposed in fluid communication with a first elongate inflation tube 36 that is in turn in fluid communication with an interior inflatable volume 38 of an inflatable portion 28 of the prosthesis 12. A second inflation port 40 may be in fluid communication with a second inflation tube (not shown) that is in turn in fluid communication with an interior volume 42 of the expandable member or balloon 24 of the delivery catheter 16. Inflation of the interior volume 42 of the inflatable portion 28 of the endovascular prosthesis 12 is illustrated in the sequence shown in FIGS. 1A-1D, discussed in more detail below.

During an interventional procedure, deployment of such an inflatable endovascular prosthesis embodiment 12 may include advancing the delivery catheter 16 over a guidewire 48 to a desired treatment site. An outer sheath 50 of the delivery catheter 16 may then be retracted to expose the endovascular prosthesis 12. In some instances, an expandable portion 24 of the delivery catheter 16 disposed within a flow lumen 26 of the endovascular prosthesis 12 may be expanded so as to define a flow lumen 26 of the device 12 during inflation. The inflatable portion 28 may then be inflated with an inflation material 52 so as to enlarge an interior volume 38 of the inflatable portion, move an outer surface 54 of the endovascular prosthesis 12 radially outward and conform the outer surface to an inner surface 56 of the body lumen 58 of the treatment site 62 as shown in FIGS. 2-5. In some cases, the inflation material 52 may be configured to set, harden or otherwise transform to a different state that will maintain the shape of the inflatable portion 28 of the endovascular prosthesis 12 in the expanded conforming configuration.

Figure 2:
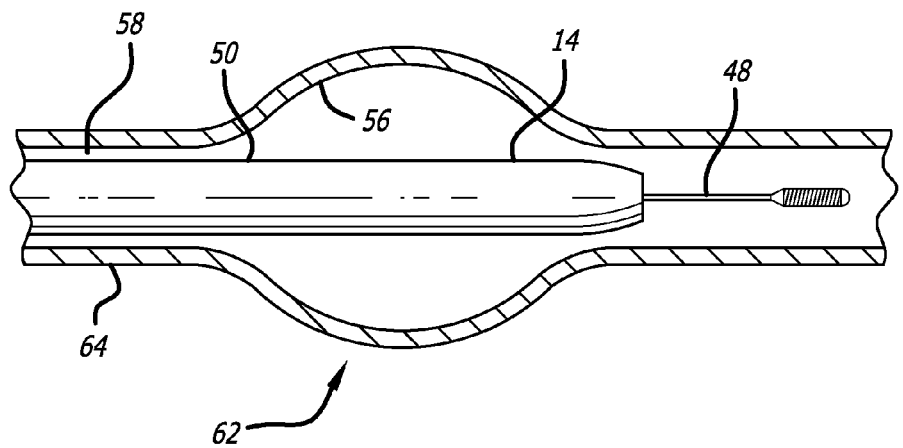
FIG. 2 illustrates an elevation view in partial section of the delivery catheter of FIG. 1 being advanced over a guidewire to an aneurysm disposed in a patient's vasculature.

FIG. 2 shows the delivery catheter 16 of the delivery system 10 of FIG. 1 being advanced into a lumen 58 of a vessel 64 of a patient's vasculature to a desired treatment site 62 that includes a radially expanded section of the vessel 64, such as the aneurysm. As shown, in some instances the delivery catheter 16 may be advanced over a guidewire 48 that includes a flexible floppy distal tip and progressively stiffer shaft that is configured to be safely advanced and steered through the lumens of the patient's vasculature and provide a guide or track for the delivery catheter 16 to safely follow. In some embodiments, the delivery catheter 16 includes a guidewire lumen 66 which extends axially from a distal end 22 of the delivery catheter 16 to a proximal end 20 of the delivery catheter 16 and which is configured to slide over an outer surface of the guidewire 48 with an inner low friction surface. For some embodiments, the guidewire lumen 66 may include the inner lumen of an elongate tubular member 68 that may extend from a distal end 22 of the delivery catheter 16 to a proximal end 20 of the delivery catheter 16. Such an elongate tubular member 68 may be constructed from or include an inner luminal surface of a low friction material including fluoropolymers such as polytetrafluoroethylene (PTFE) and the like. In some deployment methods, the guidewire 48 may first be advanced into the patient's vasculature and the delivery catheter 16 later loaded over a proximal end of the guidewire 48 and advanced distally over the guidewire 48. In some embodiments, the guidewire 48 may be preloaded into the guidewire lumen 66 of the delivery catheter 16 and the guidewire 48 and delivery catheter 16 advanced together through the vessel lumens 38 of the patient's vasculature.

Once the distal section 14 of the delivery catheter 16 of the delivery system 10 is disposed adjacent the desired treatment site 62, an outer sheath 50 of the delivery catheter 16 may be proximally retracted so as to expose the inflatable endovascular prosthesis 12 within the patient's vasculature. The outer sheath 50 of the delivery catheter 16 may be used to protect the endovascular prosthesis 12, constrain the endovascular prosthesis 12, or both, during the deployment procedure. In circumstances where the outer sheath 50 is configured to radially constrain the endovascular prosthesis 12 prior to deployment, the constraint imparted may be full or partial in that there may or may not be additional structure of the delivery catheter 16 configured to impart radial constraint on the endovascular prosthesis 12 prior to deployment.

Figure 3:
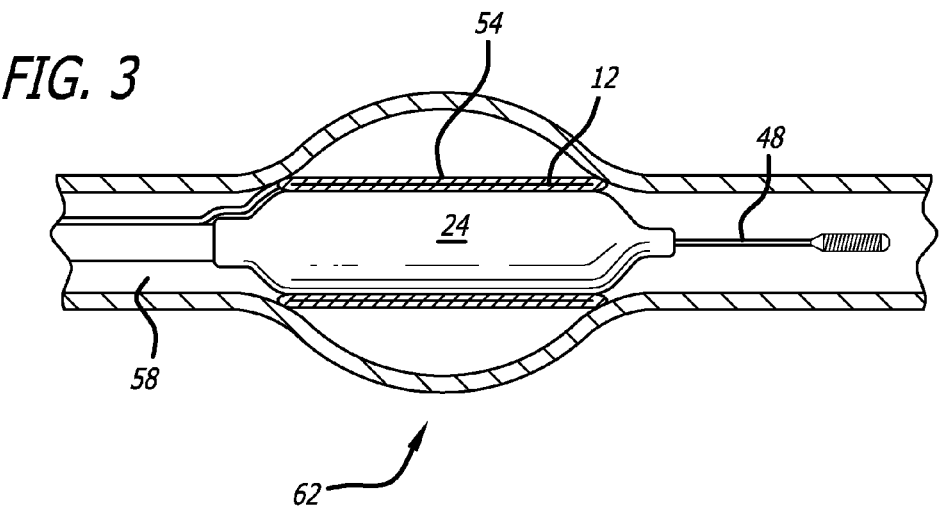
FIG. 3 illustrates the delivery catheter embodiment of FIG. 2 with an outer sheath of the delivery catheter retracted and a lumen generating inflatable member of the delivery catheter in an expanded state.

Once the outer sheath 50 is removed or the endovascular prosthesis 12 otherwise exposed, an expandable portion 24 of the delivery catheter 16 disposed within the flow lumen 26 of the endovascular prosthesis 12 may then be expanded so as to define a size and configuration of the flow lumen 26 of the endovascular prosthesis 12 as shown in FIG. 3. FIG. 3 illustrates an inflatable balloon portion 24 of the delivery catheter 16 in an inflated state which radially expands the flow lumen 26 of the prosthesis 12. For the embodiment shown, the inflatable balloon 24 of the delivery catheter 16 has a substantially cylindrical shape and is disposed about the elongate shaft 18 of the delivery catheter 16 in a substantially concentric arrangement. The inflatability of the expandable portion 24 of the delivery catheter 16 may allow the size of the flow lumen 26 to be adjusted during deployment as a function of the amount of inflation of the member 24.

Figure 4:
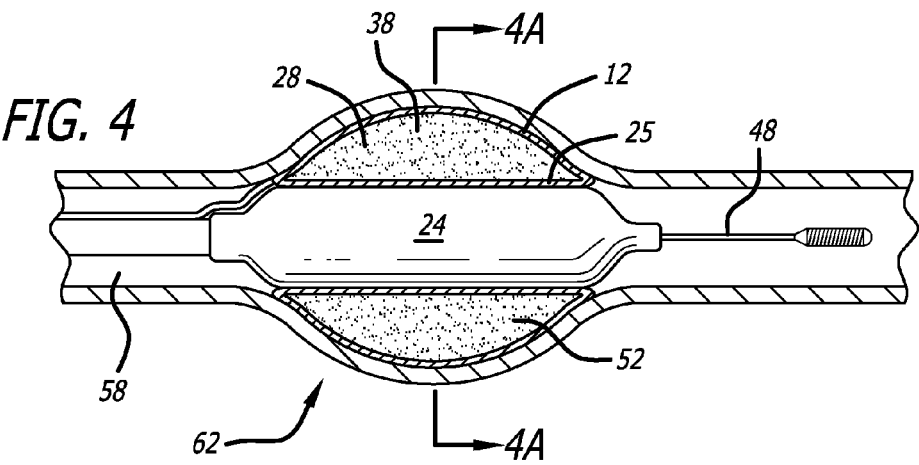
FIG. 4 shows an inflatable portion of the inflatable endovascular prosthesis embodiment inflated with an inflation material and with an outer surface of the inflatable portion conforming to an inside surface of the aneurysm of the patient's vasculature.
Figure 4A:
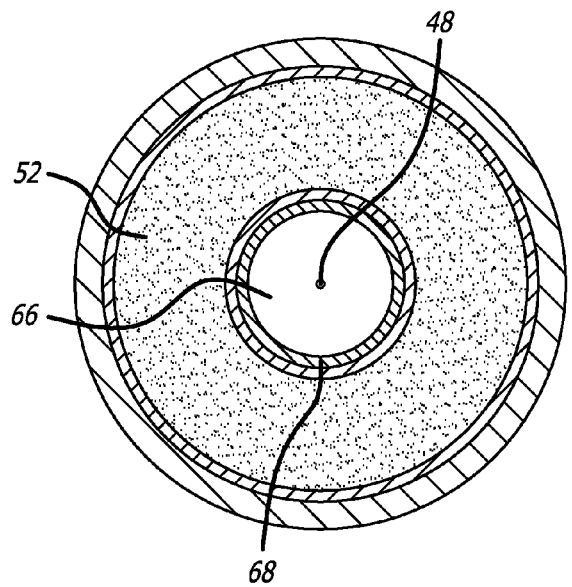
FIG. 4A is a transverse cross sectional view of the patient's vasculature, inflatable endovascular prosthesis and delivery catheter of FIG. 4 taken along lines 4A-4A of FIG. 4.

Once a desired flow lumen 26 of the endovascular prosthesis 12 is established or determined by the outside shape and configuration of the outer surface 25 of the expandable portion 24, the inflatable portion 28 of the prosthesis 12 may be inflated with inflation material 52 as shown in FIGS. 4 and 4A. The inflation material 52 may be injected under pressure into the first inflation port 34 of the proximal adapter 30 at a proximal end 20 of the delivery catheter 16 during the deployment procedure. At the time the inflation material 52 is being injected under pressure into the first inflation port 34, the inflation port 34 and proximal adapter 30 are disposed outside the patient's body and easily accessed by an operator of the system while the distal section 14 of the delivery catheter 16 and endovascular prosthesis 12 are disposed within the patient's body and vessel lumen 58. The inflation material 52 may be injected under pressure with any suitable device, such as a syringe, into the first inflation port 34. The inflation material 52 then leaves the pressurized interior volume of the syringe, or other suitable pressurized injection device 72, and travels through the first inflation port 34, through an inner lumen 74 of the first inflation tube member 36 and into the interior volume 38 of the inflatable portion 28 of the prosthesis 12.

As discussed above, the inflatable portion 28 may then be inflated with an inflation material so as to enlarge an interior volume 38 of the inflatable portion 28, move an outer surface 54 of the endovascular prosthesis 12 radially outward and conform the outer surface 54 to an inner surface 56 of the body lumen 58 of the treatment site 62. In some cases, the inflation material 52 may be configured to set, harden or otherwise transform to a different state that will maintain the shape of the inflatable portion 28 of the endovascular prosthesis 12 in the expanded conforming configuration.

As the inflation of the inflatable portion 28 of the endovascular prosthesis 12 is carried out under pressure within an interior portion of the patient's body during deployment, it may be important to have ensured that the inflatable portion 28 is free of any weaknesses or leaks prior to initiating the deployment process. This may be particularly true where the inflation material 52 is of a material other than saline or the like that will be readily absorbed by the patient's body should a leak or rupture occur. A more detailed discussion of various testing embodiments may be found below.

Figure 5:
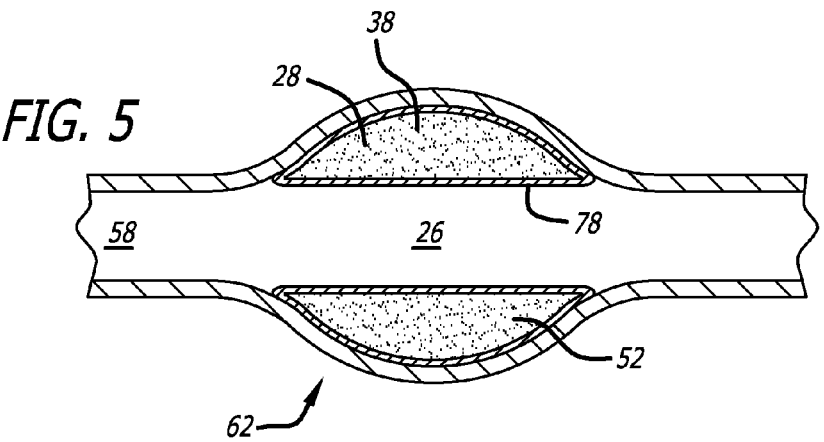
FIG. 5 illustrates the inflatable endovascular prosthesis with the delivery catheter withdrawn from the patient's vasculature.

Once the inflatable portion 28 of the endovascular prosthesis 12 has been inflated and the inflation material 52 optionally cured, hardened or otherwise set, the delivery catheter 16 may then be removed. In some instances, the expandable portion 24 of the distal section 14 of the delivery catheter 16 is first deflated and reduced in radial size prior to retraction or withdrawal of the delivery catheter 16 from the deployed endovascular prosthesis 12. This procedure may allow the expandable portion 24 to disengage with a luminal surface 78 of the newly formed flow lumen 26 of the endovascular prosthesis 12 prior to removal of the delivery catheter 16 which thereby reduces the chances of disturbing the position of the deployed endovascular prosthesis 12 during the removal. The flow lumen 26 of the endovascular prosthesis 12 as determined by the expansion member 24 of the delivery catheter 16 is shown in FIG. 5.

Referring back to FIG. 1, in some instances it may be important to test the integrity of the inflatable portion 28 of the prosthesis 12 prior to deployment but after loading onto the delivery catheter 16. Such testing methods may include methods of in vitro testing of an endovascular prosthesis 12, such as the inflatable endovascular prosthesis 12 shown. Some such testing methods may include providing or identifying an endovascular prosthesis 12 to be tested. Such an endovascular prosthesis 12, which may include an inflatable portion 28, is loaded onto a delivery system 10, such as the delivery system embodiment 10 which includes the delivery catheter 16 and the endovascular prosthesis 12. The endovascular prosthesis 12 may also be in a constrained state on the delivery catheter 16 and covered by the outer sheath 50 of the delivery catheter 16. The endovascular prosthesis 12 may be constrained with the outer tubular sheath 50 disposed over the endovascular prosthesis 12 such that an inner luminal surface 80 of the outer tubular sheath 50 restricts radial expansion of the prosthesis 12 during inflation.

In general, the delivery system 10 as shown in FIG. 1 is ready for use. More specifically, the delivery system 10 is ready for the deployment of the endovascular prosthesis 12 in a patient during a treatment procedure once the system 10 has been packaged, sterilized and shipped to a treatment center or facility. Once the prosthesis 12 is deployed within a patient at such a facility, the inflatable portion 28 of the prosthesis 12 may optionally be inflated through a fill tube 36 of the delivery catheter 12 with an inflation material 84 that may be a sterile removable inflation material 84 in some circumstances.

In some cases it may be desirable to test the prosthesis 12 for leaks after loading of the prosthesis 12 onto the delivery catheter 16 but prior to deployment within a patient's vasculature or other body passage. For such testing, an inflation material 84 may be forced under pressure into the fill tube 36 of the delivery catheter 16 through the fill port 34 of the proximal adapter 30 with a source of pressurized of inflation material 72 that may be detachably coupled to the inflation port 34 of the proximal adapter 30. The inflation material 84 may be maintained at a pressure higher than atmospheric pressure with the source of pressurized inflation material 72 with the delivery system in the deployment ready configuration as shown in FIG. 1. The inflation sequence during in vitro testing of the deployment ready system 10 is shown in FIGS. 1A-1D.

FIG. 1A shows removable fill material 84 passing through an inner lumen 37 of the inflation tube 36 as indicated by the arrow 86. FIG. 1B shows fill material 84 entering an interior volume 38 of the inflatable portion 28 of the endovascular prosthesis 12. FIG. 1C shows fill material 84 leaking from the interior volume 38 of the endovascular prosthesis 12 into a space disposed between an outside surface 25 of the inflatable member 24 and an inside surface 78 of the inflatable portion 28. FIG. 1D shows sterile removable fill material 84 leaking from the interior volume 38 of the inflatable prosthesis 12 at a distal end 22 of the delivery catheter embodiment 16 of FIG. 1.

Once the removable inflation material 84 has been injected under pressure into the interior volume 38 of the inflatable portion 28, the delivery system 10 and endovascular prosthesis 12 may be inspected for leaks of the inflation material 84. Once it has been confirmed that there are no leaks in the inflatable portion 28 of the prosthesis 12 as shown in FIGS. 1C and 1D, the removable inflation material 84 may be removed from the interior volume 38 of the inflatable portion 28. The inflation material 84 may also be removed from the interior volume 38 at any time during the procedure whether or not leaks of the inflatable portion 28 of the endovascular prosthesis 12 are detected. Once the testing has been completed and the inflation material 84 used to inflate the interior volume of the inflatable portion removed from the interior volume 38, the delivery system 10 may then be optionally packaged, sterilized and delivered to a user. The delivery system 10 may then be unpackaged and used to deploy the endovascular prosthesis 12 within a lumen 58 of a vessel 64 of the patient's vasculature as shown in FIGS. 2-5.

The inflatable portion 28 of the endovascular prosthesis 12 is shown in FIG. 1 in an uninflated state and includes the interior volume 38 which is bounded by a flexible layer 90 of material. Although the embodiment shown includes a single layer of material 90, any suitable number of layers of flexible material may be used to bind the interior volume of the inflatable portion. In addition, different types of flexible material may be used including compliant materials such as latex, parylene, polyurethanes or the like and substantially non-compliant but flexible materials such as PTFE, expanded PTFE, nylons and the like. The material of the flexible layer 90 of material may also be porous, semi-porous or non-porous. In most circumstances, the layer of flexible material bounding the interior volume of the inflatable portion 28 of the endovascular graft 12 will be impermeable or substantially impermeable to the inflation material 84 being used for the particular embodiment 12.

For embodiments of the inflatable portion 28 that include a porous or semi-porous flexible material that bounds an interior volume 38 thereof, it may be desirable to put a wetting agent into the interior volume 38 of the inflatable portion 28 prior to or simultaneously with the injection of a gaseous inflation material 84 during the testing procedure. Wetting agents such as isopropyl alcohol, and the like, may be used to saturate or partially saturate the flexible material 90 or to fill or partially fill the pores within the body of the flexible material of the inflatable portion 28 in order to prevent ingress of the inflation material 84 into and/or through the pores of the flexible material. The wetted flexible material may resist gas permeation by virtue of the surface tension of the wetting agent and pore size of the flexible material. In some instances, the testing of the endovascular prosthesis 12 may be carried out using a gas such as air, nitrogen, or the like to test for leaks. In such circumstances, the use of a wetting agent prior to inflation of the inflatable portion 28 may be required to maintain a desired pressure within the interior volume 38 if the flexible material of the inflatable portion 28 has any significant porosity. A pressure leakdown test may be used to verify that the test gas or liquid is not leaking from the interior volume 38 of the inflatable portion 28 of the graft 12. After leak checking of the graft 12, the wetting agent is removed from the interior volume 38 and graft 12 generally. The removal of the wetting agent may be facilitated with the use of a vacuum drying chamber.

In some circumstances, a removable inflation material 84 that may be used during testing may include saline, gases, such as air or inert gases, or any other material that may be readily removed from the interior volume 38, removed without leaving any undesirable residual material, or both. For some testing embodiments, the inflatable portion 28 of the prosthesis 12 may include inflating to a pressure of up to about 20 psig, more specifically, of about 1 psig to about 10 psig. The inflation pressure may be applied over a period of time in some cases of about 30 seconds to about 5 minutes, more specifically, about 1 minute to about 3 minutes.

The testing embodiments discussed above may be used with a variety of endovascular prosthesis embodiments 12. FIG. 6 shows an embodiment of a delivery system 100 including an inflatable endovascular prosthesis 102 loaded on a distal section 104 of a delivery catheter 106. As with the delivery system embodiment 10 discussed above, the delivery system 100 is shown configured for clinical use and ready to deploy the endovascular prosthesis 102 but prior to packaging and shipment. The delivery catheter 106 of the delivery system 100 includes an elongate shaft 108 having a proximal end 110, a distal end 112 and a distal section 104. A proximal adapter 114 is secured to a proximal end 110 of the elongate shaft 108 and may include one or more ports configured to communicate with the various ports and lumens of the delivery catheter 106. For example, a guidewire port 116 may be disposed in communication with a guidewire lumen 66 and an inflation port 120 may be disposed in fluid communication with an elongate inflation tube 122 that is in turn in fluid communication with an interior inflatable volume 124 of an inflatable portion of the endovascular prosthesis 102.

For the delivery system embodiment 100 shown in FIGS. 6 and 7, the inflatable endovascular prosthesis embodiment 102 may be deployed in some instances in a manner that may include some of the same operations as those of the deployment sequence discussed above with regard to the delivery system embodiment 10 of FIG. 1. The deployment sequence for the embodiment 100 of FIG. 6 may include advancing the delivery catheter 106 over a guidewire 48 to a desired treatment site 62. An outer sheath 126 of the delivery catheter 106 may then be retracted to expose the endovascular prosthesis 102 as shown in FIG. 7. In some instances, an expandable member or members 130 and 132 may be expanded to conform to an inside luminal surface of the patient's vessel 64 and provide an anchoring function to stabilize axial forces on the prosthesis 102 in some instances. The inflatable portion of the endovascular prosthesis 102 may then be inflated with an inflation material 52 so as to enlarge an interior volume of the inflatable portion.

The inflatable portion of the endovascular prosthesis 102 shown in FIGS. 7 and 8 also includes a network of inflatable channels 134 and at least one proximal cuff 136 that may be configured to provide a sealing function, structural support or both upon pressurized inflation of the inflatable portion with inflation material 52 as shown in FIG. 8. For such embodiments, inflation of the inflatable portion may move an outer surface of an inflatable cuff 136 of the endovascular prosthesis 102 radially outward and conform the outer surface of the cuff 136 to an inner surface of the body lumen 58 of the treatment site to form a seal between the outer surface and the inner surface. In some cases, the inflation material 52 may be configured to set, harden or otherwise transform to a different state that will maintain the shape of the inflatable portion of the endovascular prosthesis 102 in the expanded conforming configuration.

Some embodiments of an endovascular prosthesis 102 such as that shown in FIG. 8 may include a bifurcated main graft member formed from a supple graft material, such as ePTFE, having a main fluid flow lumen 140 therein. The main graft member 142 may also include an ipsilateral leg 144 with an ipsilateral fluid flow lumen 146 in communication with the main fluid flow lumen 140, a contralateral leg 148 with a contralateral fluid flow lumen 150 in communication with the main fluid flow lumen 140 and a network of inflatable channels 134 disposed on the main graft member 142. For some embodiments, the main graft member 142 may have an axial length of about 5 cm to about 10 cm, more specifically, about 6 cm to about 8 cm in order to span an aneurysm of a patient's aorta without engaging the patient's iliac arteries directly with the legs of the main graft member 142.

The inflatable channels of the network of inflatable channels 134 may be disposed on any portion of the main graft member 142 including the ipsilateral and contralateral legs 144 and 148. The network of inflatable channels 134 may be configured to accept a hardenable fill material 52 to provide structural rigidity to the main graft member 142 when the network of inflatable channels 134 are in an inflated state and the inflation material 52 has been cured or hardened. Radiopaque inflation material 52 may be used to facilitate monitoring of the fill process and subsequent engagement of graft extensions (not shown). The network of inflatable channels 134 may also include at least one inflatable cuff 136 disposed on a proximal portion of the main graft member 142 which is configured to seal against an inside surface of a patient's vessel 64, such as the aorta.

A proximal anchor member 152 is disposed at and secured to a proximal end of the main graft member 142. The proximal anchor member has a first self-expanding stent member 132 secured to a second self-expanding stent member 130. Both self-expanding stent members 130 and 132 have a somewhat tubular shape in some instances and may be secured together with one or more struts 154. Some embodiments of the struts 154 may have a cross sectional area that is substantially the same as or greater than a cross sectional area of proximal stent portions or distal stent portions adjacent the strut 154. Such a configuration may be useful in avoiding points of concentrated stress in the proximal anchor member 152 or struts which couple components thereof.

For some embodiments, the first self-expanding member 132 of the proximal anchor member 152 further may include a plurality of barbs 160 having sharp tissue engaging tips that are configured to extend radially outward and distally in a deployed expanded state. This configuration may be useful in order to engage tissue of an inner luminal surface of a patient's vessel 64 to mechanically anchor the prosthesis 102 to the vessel 64 in addition to the anchoring function provided by the outward radial force of the self-expanding members 130 and 132 of the proximal anchor member 152 against the inner luminal surface of the patient's vessel 64 with the prosthesis 102 in a deployed relaxed state. The second self-expanding member 130 of the proximal anchor member 152 may be secured to the proximal end 162 of the main body 142 of the prosthesis 102 with one or more struts 154 mechanically coupled to a connector ring 164 embedded in the flexible material of the main body 142 of the prosthesis 102. For some embodiments, the proximal anchor member 152 includes a 4 crown first self-expanding stent portion 132 and an 8 crown second self-expanding stent portion 130 which may be made from a superelastic alloy such as superelastic NiTi alloy.

When loaded on the delivery catheter 106, the first and second self-expanding members 130 and 132 of the proximal anchor member 152 may be radially constrained by releasable belts which are releasably held in a constraining configuration by a release member, such as a release wire 166. FIG. 7 shows the first self-expanding member 132 being radially constrained by a first releasable belt 168 and the second self-expanding member 130 radially constrained by a second releasable belt 170. The first releasable belt 168 may be released by a first release member 166 and the second releasable belt 170 may be deployed by the second release member 166. The self-expanding members 130 and 132 of the proximal anchor member 152 may only be released after the outer sheath 126 has been retracted, as shown in FIG. 7, in order to expose the endovascular prosthesis 102.

Referring back to FIG. 6, in some instances, testing methods may include providing or identifying an endovascular prosthesis to be tested, such as endovascular prosthesis 102 shown in FIG. 7. The endovascular prosthesis 102 including an inflatable portion may be loaded onto a delivery catheter 106 in a constrained state and covered by the outer sheath 126 of the delivery catheter 106. In some cases, the endovascular prosthesis 102 may optionally be constrained or partially constrained with the outer tubular sheath 126 disposed over the endovascular prosthesis 102 such that an inner luminal surface of the outer tubular sheath 126 restricts radial expansion of the prosthesis 102 during inflation. The delivery system 100 as shown in FIG. 6 is essentially ready for use for the deployment of the endovascular prosthesis 102 once the system has been sterilized. The inflatable portion of the prosthesis 102 may then be inflated through a fill tube 122 of the delivery catheter 106 with an inflation material 84 that may be a sterile removable inflation material in some circumstances.

During testing, the inflation material 84 may be forced under pressure into the fill tube 122 of the delivery catheter 106 through the fill port 120 of the proximal adapter 114 with a source of pressurized of inflation material 72 that may be detachably coupled to the inflation port 120 of the proximal adapter 114. The inflation process discussed here and in the procedures discussed above, may be carried out in vitro on a lab bench or any other suitable work space. Inflation of the inflatable portion, including the network of inflatable channels 134, of the endovascular prosthesis 102 through the fill tube 122 of the delivery catheter 106 is optional, and may be carried out by other methods. However, this technique may be used not only to test the integrity of the inflatable portion of the endovascular prosthesis, but the integrity of the fill port 120, fill tube 122, inflatable portion 134 and 136 and all connections therebetween. The inflation material 84 may be maintained at a pressure higher than ambient pressure with the source of pressurized inflation material 72 with the delivery system 100 in the deployment ready configuration.

Once the inflation material 84 has been injected under pressure into the interior volume 124 of the inflatable portion, the delivery system 100 as a whole including the delivery catheter 106 and endovascular prosthesis 102 may be inspected for leaks of the inflation material. Once it has been confirmed that there are no leaks in the inflatable portion of the prosthesis 102, the inflation material 84 may be removed from the interior volume 124 of the inflatable portion 134 and 136. The inflation material 84 may also be removed from the interior volume 124 at any time during the procedure whether or not leaks of the inflatable portion 134 and 136 of the endovascular prosthesis 102 are detected. Once the testing has been completed and the inflation material 84 used to inflate the interior volume 124 of the inflatable portion removed from the interior volume 124, the delivery system 100 may then be optionally packaged, sterilized and delivered to a user. The delivery system 100 may then be unpackaged and used to deploy the endovascular prosthesis 102 within a lumen of a vessel 64 of the patient's vasculature as discussed above.

The inflatable portion 134 and 136 of the endovascular prosthesis 102 is shown in FIG. 7 in an uninflated state and includes the interior volume 124 which is bounded by a flexible layer 172 of material. Any suitable number of layers of flexible material 172 may be used to bound the interior volume 124 of the inflatable portion. In addition, different types of flexible material may be used including compliant materials such as latex, parylene, polyurethanes or the like and substantially non-compliant but flexible materials such as PTFE, expanded PTFE, nylons and the like. The material of the flexible layer 172 of material may also be porous, semi-porous or non-porous depending on the type of inflation material 84 used to inflate the inflatable portion. In most circumstances, the layer of flexible material 172 bounding the interior volume 124 of the inflatable portion of the endovascular graft 102 will be impermeable or substantially impermeable to the inflation material 84 being used for the particular embodiment.

For embodiments of the inflatable portion that include a porous or semi-porous flexible material that bounds an interior volume 124 thereof, it may be desirable to put a wetting agent into the interior volume of the inflatable portion prior to or simultaneously with the injection of the inflation material 84 during the testing procedure. Wetting agents such as isopropyl alcohol, and the like, may be used to coat or partially coat an interior surface of the flexible material 172 or to fill or partially fill the pores within the body of the flexible material 172 of the inflatable portion in order to prevent ingress of the inflation material into the pores or to make the flexible material less porous. In some instances, the testing of the endovascular prosthesis 102 may be carried out using a gas such as air, nitrogen, or the like to test for leaks. In such circumstances, the use of a wetting agent prior to inflation of the inflatable portion may be required to maintain a desired pressure within the interior volume 124 if the flexible material 172 of the inflatable portion has any significant porosity.

In some circumstances, the removable inflation material 84 that may be used during testing may include saline, gases, such as air or inert gases, or any other material that may be readily removed from the interior volume 124, removed without leaving any undesirable residual material, or both. For some testing embodiments, the inflatable portion of the prosthesis 102 may include inflating to a pressure of up to about 20 psig, more specifically, of about 1 psig to about 10 psig. The inflation pressure may be maintained over a period of time in some cases of about 15 seconds to about 10 minutes, more specifically, about 1 minute to about 3 minutes.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although embodiments of the invention have been described in substantial detail with reference to one or more specific embodiments, those of ordinary skill in the art will recognize that changes may be made to the embodiments specifically disclosed in this application, yet these modifications and improvements are within the scope and spirit of the invention.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this invention.

Certain embodiments of the invention are set forth in the claim(s) that follow(s).

What is claimed is:

1. A method of in vitro testing of an endovascular prosthesis, comprising:
   providing an endovascular prosthesis including an inflatable portion which is loaded onto a delivery system, the inflatable portion of the endovascular prosthesis being in an uninflated state and including an interior volume bounded by at least one flexible layer of material;
   inflating an inflatable portion of the prosthesis through a fill tube with a sterile removable inflation material and maintaining the fill material at a pressure higher than ambient pressure with the delivery system in a deployment ready configuration;
   inspecting the delivery system and endovascular prosthesis for leaks of fill material;
   confirming that there are no leaks in the inflatable portion of the prosthesis; and
   removing the inflation material from the inflatable portion.

2. The method of claim 1 wherein an interior volume of the inflatable portion of the endovascular prosthesis is surrounded by at least one layer of porous flexible material, and further comprising filling the pores of the porous flexible material by wetting the porous flexible material of the inflatable portion with a wetting agent and then inflating the inflatable portion with fill material.

3. The method of claim 2 wherein inflating the inflatable portion of the endovascular prosthesis with a sterile removable inflation material comprises inflating the inflatable portion of the prosthesis with isopropyl alcohol.

4. The method of claim 2 wherein inflating the inflatable portion of the endovascular prosthesis with a sterile removable inflation material comprises inflating the inflatable portion of the prosthesis with saline.

5. The method of claim 1 wherein inflating the inflatable portion of the prosthesis comprises inflating to a pressure of about 1 psig to about 10 psig.

6. The method of claim 1 wherein the inflatable portion of the endovascular prosthesis comprises a toroidal configuration.

7. The method of claim 1 wherein the at least one flexible layer of material of the inflatable portion comprises ePTFE.

8. The method of claim 1 wherein loading the endovascular prosthesis onto a delivery system comprises radially constraining the endovascular prosthesis with an outer tubular sheath disposed over the endovascular prosthesis such that an inner luminal surface of the outer tubular sheath restricts radial expansion of the prosthesis during inflation.

9. The method of claim 1 further comprising deploying the endovascular prosthesis at a target site within a patient's vasculature.

10. A method of in vitro testing of an endovascular prosthesis, comprising:
    providing a double walled endovascular prosthesis including a toroidal inflatable portion which is loaded onto a delivery system, the inflatable portion of the endovascular prosthesis being in an uninflated state and including an interior volume bounded by at least one flexible layer of material;
    inflating an inflatable portion of the prosthesis through a fill tube with a sterile removable inflation material and maintaining the inflation material at a pressure higher than ambient pressure with the delivery system in a deployment ready configuration;
    inspecting the delivery system and endovascular prosthesis for leaks of inflation material;
    confirming that there are no leaks in the inflatable portion of the prosthesis; and
    removing the inflation material from the inflatable portion.

11. The method of claim 10 wherein an outer wall of the double walled endovascular prosthesis includes a compliant outer wall portion.

12. The method of claim 10 wherein an outer wall of the double walled endovascular prosthesis includes a non-compliant outer wall portion.

13. The method of claim 10 wherein loading the endovascular prosthesis onto a delivery system comprises radially constraining the endovascular prosthesis with an outer tubular sheath disposed over the endovascular prosthesis such that an inner luminal surface of the outer tubular sheath restricts radial expansion of the prosthesis during inflation.

14. The method of claim 10 wherein the flexible layer of material that bounds the interior volume of the inflatable portion comprises parylene.

15. The method of claim 10 further comprising deploying the endovascular prosthesis at a target site within a patient's vasculature.

16. A method of in vitro testing of an endovascular prosthesis, comprising:
    providing an endovascular prosthesis including an inflatable portion which is loaded onto a delivery system, the inflatable portion of the endovascular prosthesis being in an uninflated state and including an interior volume bounded by at least one flexible layer of material, a longitudinal inflation channel and an inflatable cuff disposed at a proximal end of the prosthesis and including an interior volume in fluid communication with an interior volume of the longitudinal inflation channel;
    inflating an inflatable portion of the prosthesis through a fill tube with a sterile removable inflation material and maintaining the inflation material at a pressure higher than atmospheric pressure with the delivery system in a deployment ready configuration;
    inspecting the delivery system and endovascular prosthesis for leaks of inflation material;
    confirming that there are no leaks in the inflatable portion of the prosthesis; and
    removing the inflation material from the inflatable portion.

17. The method of claim 16 wherein an interior volume of the inflatable portion of the endovascular prosthesis is surrounded by at least one layer of porous flexible material and further comprising filling the pores of the porous flexible material with a wetting agent and then inflating the inflatable portion of the prosthesis with inflation material for leak testing.

18. The method of claim 17 wherein inflating the inflatable portion of the endovascular prosthesis with a sterile removable fill material comprises inflating the inflatable portion of the prosthesis with isopropyl alcohol.

19. The method of claim 17 wherein inflating the inflatable portion of the endovascular prosthesis with a sterile removable fill material comprises inflating the inflatable portion of the prosthesis with saline.

20. The method of claim 16 wherein inflating the inflatable portion of the prosthesis comprises inflating to a pressure of about 1 psig to about 20 psig.

21. The method of claim 16 wherein loading the endovascular prosthesis onto a delivery system comprises radially constraining the endovascular prosthesis with an outer tubular sheath disposed over the endovascular prosthesis such that an inner luminal surface of the outer tubular sheath restricts radial expansion of the prosthesis during inflation.

22. The method of claim 16 wherein the at least one flexible layer of material of the inflatable portion comprises ePTFE.

23. The method of claim 16 further comprising deploying the endovascular prosthesis at a target site within a patient's vasculature.

\* \* \* \* \*